July 28, 1970 J. W. PATTERSON Plant Pat. 2,984
ROSE
Filed July 29, 1968
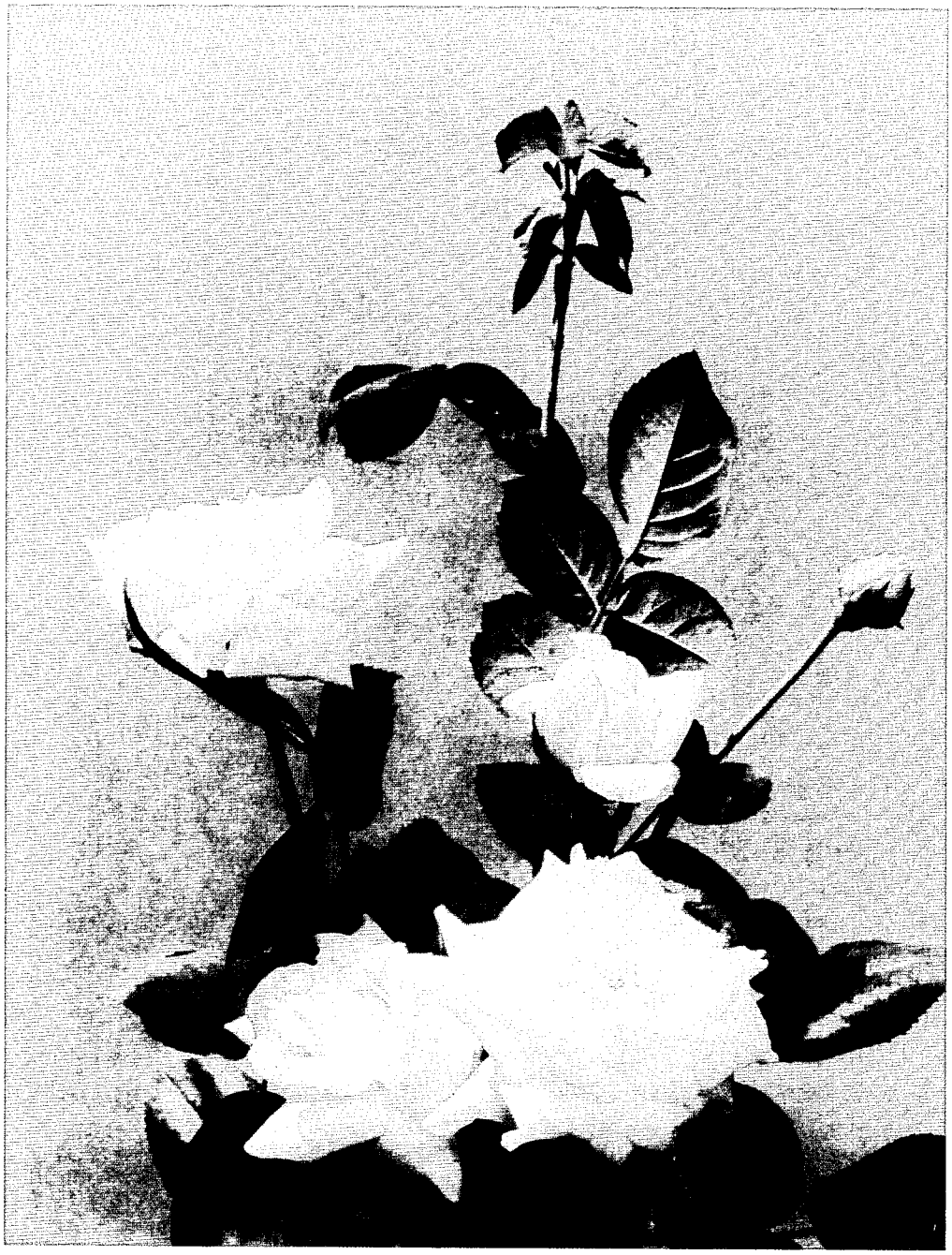

United States Patent Office

Plant Pat. 2,984
Patented July 28, 1970

2,984
ROSE PLANT

John W. Patterson, 6518 Kernel, Houston, Tex. 77017

Filed July 29, 1968, Ser. No. 748,570
Int. Cl. A01h 5/00
U.S. Cl. Plt.—15 1 Claim The present invention relates to a new and distinct variety of rose plant of the hybrid tea class which was originated by me by crossing the variety "Ma Perkins" (Plant Pat. No. 1,143) with the variety "Peace" (Plant Pat. No. 591).

The primary objective of this breeding was to produce a new rose variety which bears flowers of improved color and to improve the longevity of cut flowers. The objective also was to produce a good show bloom on a strong stem and also one which will keep on refrigeration for a long time. The objectives were substantially achieved by the following characteristics which are outstanding in the new variety and which distinguish it from its parents, as well as from all other varieties of which I am aware:

(1) Good growing compact bush;

(2) Large flowers borne on strong stems of medium length;

(3) Moderate flower fragrance;

(4) Good flower form;

(5) Average disease resistance, particularly with respect to mildew;

(6) Good keeping qualities of the flowers as cut flowers;

(7) A beautiful distinctive general color tonality of the flowers corresponding to Indian Yellow in newly opened flowers, and to near Lemon Yellow in three-days open flowers.

In comparison with its seed parent "Ma Perkins" the new variety has more glossy foliage; bears larger flowers of a definite entirely different color; flowers are of better form and have better keeping qualities as cut flowers.

As compared with the pollen parent "Peace" the new variety is a better grower, and is also definitely distinct therefrom, as evidenced by the fact that the blooms are solid yellow when open, whereas "Peace" is a yellow and pink blend.

Asexual reproduction of my new variety by budding, as performed at Houston, Tex., and also at Tyler, Tex., shows that the foregoing characteristics of my new variety come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society:

Type: Bush; seedling.
Class: Hybrid tea.
Breeding: Seedling.
*Seed parent.*—"Ma Perkins."
*Pollen parent.*—"Peace."
Propagation: Holds its distinguishing characteristics through succeeding propagations by budding.

FLOWER

Locality where grown and observed: Houston, Tex.
Blooming habit: Recurrent—continuous through season.
Flowers borne: Singly to stem (occasionally more than one); on strong stems of medium length.

Quantity of bloom: Abundant, outdoors.
Fragrance: Moderate, nature-tea.
Bud:
*Peduncle.*—Long; strong; erect. Moderately smooth; soft prickles. Color—Scheeles Green, Plate 860/2, page 175.
*Before calyx breaks.* — Size — large. Form — long, pointed; with foliaceous appendages on the surface of the bud; with some foliaceous parts extending beyond tips of buds. Color—Scheeles Green, Plate 860/3, page 175, with foliaceous tips slightly overlaid with Indian Lake, Plate 826/1, page 170.
*As calyx breaks.*—Color (outside of petal)—Lemon Yellow, Plate 4/2, page 4, with tinges of Geranium Lake, Plate 20/2, page 20, showing on edges and tips of petals.
*As first petal opens.*—Size—average to large. Form—long. Color: outside—base of Buttercup Yellow, Plate 5/1, page 5, changing to Lemon Yellow, Plate 4/2, page 4; inside—base Lemon Yellow, Plate 4/2, page 4, changing to Aureolin, Plate 3/2, page 3.
*Opening.*—Opens up well. Opens slowly keeping shape well in cool weather. Opens faster in hot weather.
Bloom:
*Size (when fully open).*—Large; from 4 inches to 5 inches.
*Petalage.*—Double; from 35 to 45 petals; arranged regularly.
*Form.*—Long pointed and high centered at first, later petals slightly reflexing at maturity.
Petals:
*Texture.*—Thick; leathery; and smooth.
*Shape.*—Outer, intermediate and inner petals all obovate with rounded apex.

This description of a newly opened flower was made from a rose grown outdoors during the month of July at Houston, Tex.

*Color.*—Outer petal: outside surface—base of petal Aureolin, Plate 3, page 3, gradually changing through Aureolin, Plate 3/1 to Aureolin, Plate 3/2, page 3, at top of petal; inside surface—base of petal, Aureolin, Plate 3, page 3, changing through Aureolin, Plate 3/1, to Aureolin, Plate 3/2, page 3, in remainder of petal. Intermediate petal: outside surface—Lemon Yellow, Plate 4/2, page 4; inside surface—Lemon Yellow, Plate 4/2, changing to Lemon Yellow, Plate 4/3, page 4. Inner petal: outside surface—base Indian Yellow, Plate 6/1, changing to Indian Yellow, Plate 6/2, page 6; inside surface—Buttercup Yellow, Plate 5/2, page 5.

This description was made from a rose that was open for three days outdoors during the month of July at Houston, Tex.

*Color.*—Outer petal: outside surface—base about ⅓ of petal length, Aureolin, Plate 3/1, page 3. Remainder of petal changing to Aureolin, Plate 3/2, and Plate 3/3, page 3; inside surface—near Buttercup Yellow, Plate 5/3, page 5. Intermediate petal: outside surface—near Lemon Yellow, Plate 4/2, page 4; inside surface—Lemon Yellow, Plate 4/2, to Lemon Yellow, Plate 4/3, page 4. Inner petal: outside surface—near Buttercup Yellow, Plate 5/2, page 5; inside surface—near Lemon Yellow, Plate 4/2, page 4.

*General color effect.*—Newly opened flower—near Indian Yellow, Plate 6/2, page 6. Three days open—near Lemon Yellow, Plate 4/2, page 4.

*Behavior of petals.*—Drop off cleanly; not particularly affected by weather.

*Flower longevity.*—On bush in garden—3 to 4 days in July. Cut flowers grown outdoors and kept inside at room temperature 3 to 4 days in July.

REPRODUCTIVE ORGANS

Stamens: Many; arranged irregularly about pistils.

Filaments: Some short and some long; most with anthers. Color—Cardinal Red, Plate 822/1, page 168.

Anthers: Medium size; open at various times. Color—near Spiraea Red, Plate 025, page 112.

Pollen: Sparse. Color—near Yellow Ochre, Plate 07/2, page 101.

Pistils: Average amount.

Styles: Average length; uneven and bunches.

Stigma: Color—near Delft Rose, Plate 020, page 108.

Ovularies: Most enclosed in receptacle.

Hips: Few; globular; smooth; walls thick and fleshy.

Sepals: Permanent; long length; narrow and pointed. Color: inside—near Fern Green, Plate 0862, page 186, overlaid with white fuzz; outside—Scheeles Green, Plate 860, page 175.

Seeds: Average number to many; medium size; from 15 to 25 in number.

PLANT

Foliage:

*Leaves.*—Compound of usually 5 leaflets; moderate amount; glossy; medium large size.

*Leaflets.*—Shape—ovate. Apex—acute. Base—round. Margin serrate.

*Color.*—Mature: upper surface, between Spinach Green, Plate 0960, page 187, and Ivy Green, Plate 0001060/3, page 200; under surface, near Spinach Green, Plate 0960/2, page 187. Young: upper surface—near Spinach Green, Plate 0960/1, page 187; under surface—near Spinach Green, Plate 0960/3, page 187, slightly overlaid with Indian Lake, Plate 826/1, page 170.

*Rachis (the supporting stem of the compound leaf).*—Medium heavy. Upper side—almost smooth; grooved. Under side—prickly.

*Stipules.*—Medium length; narrow; with short points out at an angle less than 45°.

Growth:

*Habit.*—Bush; upright; compact.

*Growth.*—Vigorous.

*Canes.*—Medium diameter; strong.

*Main stems.*—Color—Spinach Green, Plate 0960/3, page 187. Thorns—several; short length; points straight; with narrow base; color—near Willow Green, Plate 00862, page 199. Prickles and Hairs—none.

*Branches.*—Color—Scheeles Green, Plate 860/1, page 175. Thorns—several; short length; straight to slightly hooked downward; with narrow base; color—near Erythrite Red, Plate 0027, page 190. Some small prickles. Hairs—none.

*New shoots.*—Color—Scheeles Green, Plate 860/2, page 175. Large prickles—several to many; short length; with moderately long, narrow base; color—Lettuce Green, Plate 861/3, page 176, slightly overlaid with Erythrite Red, Plate 0027/1, page 190. Some small prickles; color—Lettuce Green, Plate 861/2, page 176.

I claim:

1. A new and distinct variety of rose plant of the hybrid tea class, substantially as herein shown and described, characterized particularly as to novelty by the combination of good growing and flower producing habits, glossy, green foliage, large flowers which are borne on strong stems, good flower form, especially in newly opened flowers, moderate flower fragrance; better than average disease resistance, particularly with respect to mildew, an attractive general color tonality of the flowers corresponding to Indian Yellow in the newly opened flowers, and to near Lemon Yellow in the three days open flowers, and good keeping qualities of flowers as show blooms.

No references cited.

ROBERT E. BAGWILL, Primary Examiner